(12) United States Patent
Lubar et al.

(10) Patent No.: US 10,555,862 B2
(45) Date of Patent: Feb. 11, 2020

(54) TABLE ARMBOARD ADJUSTMENT ASSEMBLY

(71) Applicant: General Electric Company, Schenectady, NY (US)

(72) Inventors: Eric Jeffrey Lubar, Milwaukee, WI (US); Jiaqi Li, Brookfield, WI (US); Jason Philps, Hartland, WI (US); Paul Jason Krueger, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 401 days.

(21) Appl. No.: 15/389,349

(22) Filed: Dec. 22, 2016

(65) Prior Publication Data

US 2018/0177468 A1 Jun. 28, 2018

(51) Int. Cl.
| | |
|---|---|
| *A61G 13/12* | (2006.01) |
| *A61B 6/04* | (2006.01) |
| *A61G 7/075* | (2006.01) |
| *A61G 13/06* | (2006.01) |
| *A61G 13/10* | (2006.01) |

(52) U.S. Cl.
CPC ........ *A61G 13/1235* (2013.01); *A61B 6/0407* (2013.01); *A61G 7/075* (2013.01); *A61G 13/06* (2013.01); *A61G 13/104* (2013.01)

(58) Field of Classification Search
CPC ..... A61B 6/0407; A61B 6/032; A61B 5/0555; A61G 7/0507; A61G 7/0508; A61G 7/0509; A61G 7/051; A61G 7/065; A61G 7/075; A61G 13/12; A61G 13/1205; A61G 13/1235; A61G 13/124; A61G 13/06; A61G 13/104; A61F 5/3723
See application file for complete search history.

(56) References Cited

U.S. PATENT DOCUMENTS

| 152,411 A | 6/1874 | Quinsac |
|---|---|---|
| 612,373 A | 10/1898 | Allison |

(Continued)

FOREIGN PATENT DOCUMENTS

| AU | 8084775 A | 11/1976 |
|---|---|---|
| AU | 4168585 A | 10/1985 |

(Continued)

OTHER PUBLICATIONS

Kren, L. et al., "Getting up to speed with wrap-spring clutch/brakes: No-slip clutch/brakes keep loads and drives synced up," Machine Design Website, Available Online at http://machinedesign.com/mechanical-drives/getting-speed-wrap-spring-clutchbrakes, Jan. 25, 2007, 7 pages.

(Continued)

*Primary Examiner* — David R Hare
(74) *Attorney, Agent, or Firm* — McCoy Russell LLP

(57) ABSTRACT

Methods and systems are provided for an armboard adjustment assembly for a patient support table. In one embodiment, an armboard adjustment assembly is configured to retain a rotational position of an armboard of a patient support table via a plurality of one-way clutches, and in another embodiment the armboard adjustment assembly is configured to retain the rotational position of the armboard via a pair of friction pads. In this way, the armboard may be moved into a continuous plurality of positions between a fully lowered position and a fully raised position.

11 Claims, 10 Drawing Sheets

(56) References Cited

U.S. PATENT DOCUMENTS

| | | | |
|---|---|---|---|
| 634,306 A | 10/1899 | Morrissey | |
| 1,061,309 A | 5/1913 | McQuown | |
| 1,069,864 A | 8/1913 | Dillich | |
| 1,199,064 A | 9/1916 | Foyer | |
| 1,227,704 A | 5/1917 | Ulrich | |
| 1,237,572 A | 8/1917 | Stickney | |
| 1,271,453 A | 7/1918 | Elzey | |
| 1,291,937 A | 1/1919 | Lange | |
| 1,308,511 A | 7/1919 | Steele | |
| 1,318,505 A | 10/1919 | Rabczynski | |
| 2,041,196 A | 5/1936 | Liska | |
| 2,449,678 A | 9/1948 | Stallcup | |
| 2,605,152 A * | 7/1952 | Krewson | A61G 13/12 108/152 |
| 2,642,250 A * | 6/1953 | Kasnowich | A61G 13/12 108/49 |
| 2,895,775 A * | 7/1959 | McDonald | A61G 13/12 5/618 |
| 3,020,909 A * | 2/1962 | Stevens | A61G 13/0036 5/623 |
| 3,046,072 A * | 7/1962 | Douglass, Jr. | A61G 13/12 5/623 |
| 3,124,328 A | 3/1964 | Kortsch | |
| 3,204,948 A | 9/1965 | Denton | |
| 4,698,837 A * | 10/1987 | Van Steenburg | A61B 6/0442 378/208 |
| 5,135,210 A * | 8/1992 | Michelson | A61G 13/12 5/623 |
| 5,287,575 A * | 2/1994 | Allen | A61G 13/101 248/231.41 |
| 5,444,882 A * | 8/1995 | Andrews | A61G 13/00 5/618 |
| 5,742,962 A * | 4/1998 | Yoshino | A61B 6/0421 5/600 |
| 5,771,512 A | 6/1998 | Kurakake et al. | |
| 5,887,948 A | 3/1999 | Hannes | |
| 5,940,912 A * | 8/1999 | Keselman | A61G 13/1235 297/411.35 |
| 6,635,813 B2 | 10/2003 | Campling | |
| 6,663,055 B2 * | 12/2003 | Boucher | A61G 13/12 248/118 |
| 6,808,493 B1 | 10/2004 | Bookwalter et al. | |
| 7,322,060 B2 * | 1/2008 | Kirn | A61G 13/12 297/411.35 |
| 7,452,032 B1 * | 11/2008 | Roleder | A47C 7/54 297/182 |
| 8,617,166 B2 | 12/2013 | Hanson et al. | |
| 8,875,329 B2 * | 11/2014 | Gomez | A61G 13/1235 128/845 |
| 9,572,741 B2 * | 2/2017 | Weaver | A61F 5/3723 |
| 2001/0027711 A1 | 10/2001 | Campling | |
| 2002/0013966 A1 * | 2/2002 | Heimbrock | A61G 7/00 5/600 |
| 2005/0187459 A1 | 8/2005 | Trequattrini et al. | |
| 2008/0201850 A1 | 8/2008 | Brito et al. | |
| 2010/0018537 A1 * | 1/2010 | Soto | A61G 13/12 128/845 |
| 2016/0331617 A1 * | 11/2016 | Stryker | A61G 7/1044 |

FOREIGN PATENT DOCUMENTS

| | | |
|---|---|---|
| AU | 3983285 A | 3/1986 |
| AU | 699247 B2 | 11/1998 |
| CN | 1914515 A | 2/2007 |
| CN | 2933291 Y | 8/2007 |
| CN | 201019759 Y | 2/2008 |
| CN | 102401871 A | 4/2012 |
| CN | 1914515 B | 1/2013 |
| CN | 203455441 U | 2/2014 |
| DE | 10324038 A1 | 12/2004 |
| DE | 102008050953 A1 | 4/2010 |
| EP | 1143408 A2 | 10/2001 |
| EP | 1143408 BI | 10/2005 |
| GB | 2361089 A | 10/2001 |
| GB | 2361089 B | 4/2004 |
| GB | 2529213 A | 2/2016 |
| IN | 200705072 P4 | 5/2008 |
| JP | H02224645 A | 9/1990 |
| JP | 4594329 B2 | 12/2010 |
| JP | 5318567 B2 | 10/2013 |
| KR | 20080022098 A | 3/2008 |
| KR | 101338569 B1 | 12/2013 |
| WO | 8203320 A1 | 10/1982 |
| WO | 2005076026 A1 | 8/2005 |
| WO | 2011063281 A1 | 5/2011 |

OTHER PUBLICATIONS

"Power. Simplicity. Cardiac MR," GE Healthcare Product Brochure, Retrieved Online at www.gehealthcare.com, Available as Early as Jan. 1, 2011, 20 pages.

"One way clutch 5 (spring)" YouTube Website, Available Online at www.youtube.com/watch?v=wcYKttiovDA, Aug. 4, 2012, 1 page.

"Wrap Spring Clutches and Clutch/Brakes," Warner Electric Brochure, Available Online at www.altraliterature.com//-/media/Files/Literature/Brand/warner-electric/catalogs/p-1310-we.ashx, Website Available as Early as Oct. 2013, 44 pages.

Leone, M., "Selecting a Wrap Spring Clutch/Brake for Optimal Performance and Long Service Life," Thomson Industries, Inc. Website, Available Online at http://www.thomsonlinear.com/downloads/articles/Selecting_Wrap_Spring_Clutch_Brake_for_Optimal_Performance_taen.pdf, Available as Early as May 14, 2015, 11 pages.

* cited by examiner

TABLE ARMBOARD ADJUSTMENT ASSEMBLY

FIELD

Embodiments of the subject matter disclosed herein relate to patient support tables, and more particularly, to patient support tables for imaging the patient.

BACKGROUND

Imaging systems, such as a magnetic resonance imaging (MRI) system, may include a patient support table configured to support the body of a patient (or other object to be imaged). The patient support table may include one or more rotatable boards positioned along opposite sides of the patient support table, sometimes referred to as armboards. Each armboard may normally be in a fully lowered position relative to a top portion of the patient support table, and each armboard may be rotated separately into a partially raised position in order to provide additional support for the body of the patient or a rotated into a fully raised position in order to prevent a movement of the patient away from the table.

In order to adjust the position of the armboards, an operator of the patient support table typically actuates a handle of the corresponding armboard while pulling the armboard upward or pushing the armboard downward. Actuation of the handle releases a locking mechanism of the armboard from a detent, thereby enabling rotation of the armboard relative to the patient support table. Each armboard is typically configured to lock into three different positions: a fully lowered position, a partially raised position, and a fully raised position.

BRIEF DESCRIPTION

In some situations, a load (such as an arm of the patient) may be supported by the armboards and may increase an effective weight of one or more of the armboards. This may result in an increased amount of force needed to release the locking mechanism from the detent.

In one embodiment, a system for a patient support table comprises: a board along a side of the table; and an actuation device configured to adjust a position of the board relative to the patient support table, the board adjustable by the board actuation device from a default position through at least three locked positions, wherein the board actuation device is configured to allow movement of the board from the default position to each and any of the at least three undefined locked positions with only a single actuation input. In this way, the board may be adjusted to a plurality of variable positions in order to accommodate a variety of imaging conditions and systems without requiring increased actuation force even when the board has increased loading.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 1-2 and FIGS. 4-10 are shown to scale, though other relative dimensions may be used.

DETAILED DESCRIPTION

Figure 1:
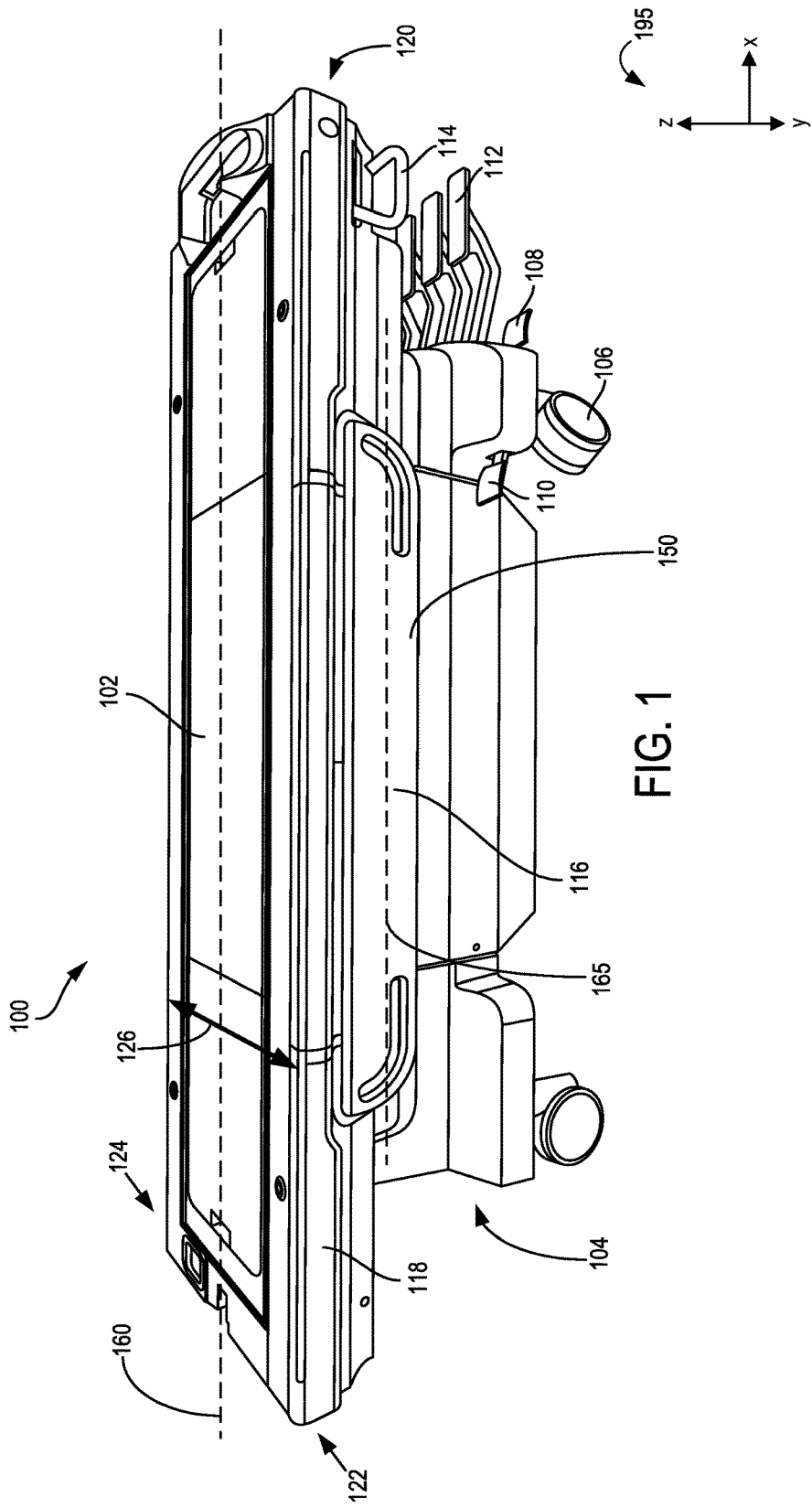
FIG. 1 shows a perspective view of a patient support table with boards of the table adjusted to a fully lowered position.

The following description relates to various embodiments of patient support tables. In particular, systems and methods are provided for a board adjustment assembly for a table. An example of a patient support table that may include a board adjustment assembly is provided in FIGS. 1-2. A board of the table is pivotally mounted to the table, and a rotational position of the board relative to a base of the table is adjustable via the board adjustment assembly. Each board of the table may be adjusted to a plurality of positions between a fully lowered position and a fully raised position, as shown schematically by FIG. 3. In a first embodiment of the board adjustment assembly shown by FIGS. 4-5, the board adjustment assembly includes two one-way clutches coupled at opposite ends of a connecting rod and positioned beneath the board. The one-way clutches are configured to allow the board to pivot in an upward direction relative to the base of the table. The one-way clutches do not allow the board to pivot in a downward direction relative to the base unless a clutch release of each one-way clutch is actuated via rotation of the connecting rod. In some examples, such as the second embodiment of the board adjustment assembly shown by FIG. 6 or the third embodiment shown by FIG. 7, the clutch release of one or more of the clutches is actuated via a cable coupled to a lever of the board. In other examples, such as the fourth embodiment shown by FIGS. 8-10, the board adjustment assembly includes a pair of friction pads that press against a braking surface in order to retain the rotational position of the board relative to the base of the table. The friction pads do not press against the braking surface while a lever of the board is actuated, thereby allowing adjustment of the rotational position of the board.

In one example, the patient support table may be a table suitable for a magnetic resonance imaging (MRI) system. It should be understood that the present techniques may also be useful when applied to other tables used in medical environments, such as computerized tomography (CT) tables, hospital patient transfer tables, and so forth. The present discussion of an MRI table used to support a patient for imaging via an MRI imaging modality is provided merely as an example of one suitable table. In some examples, such as the example of the MRI table, increasing the number of possible positions of the board via the board adjustment assembly according to the examples described below with reference to FIGS. 1-10 may enable an operator of the table to increase or decrease an effective width of the table. In one example, the effective width of the table may be increased during transportation of a patient and decreased during imaging of the patient via the MRI system. In another example, the effective width may be decreased while the table is transported (e.g., moved) without the patient on the table. In this way, the effective width of the table may be adjusted such that the table fits within a hospital elevator or through a door of a scan room of the MRI system (for example). Similarly, the width of the table may be adjusted to fit within a scan room of a variety of systems, such as those described above.

Figure 2:
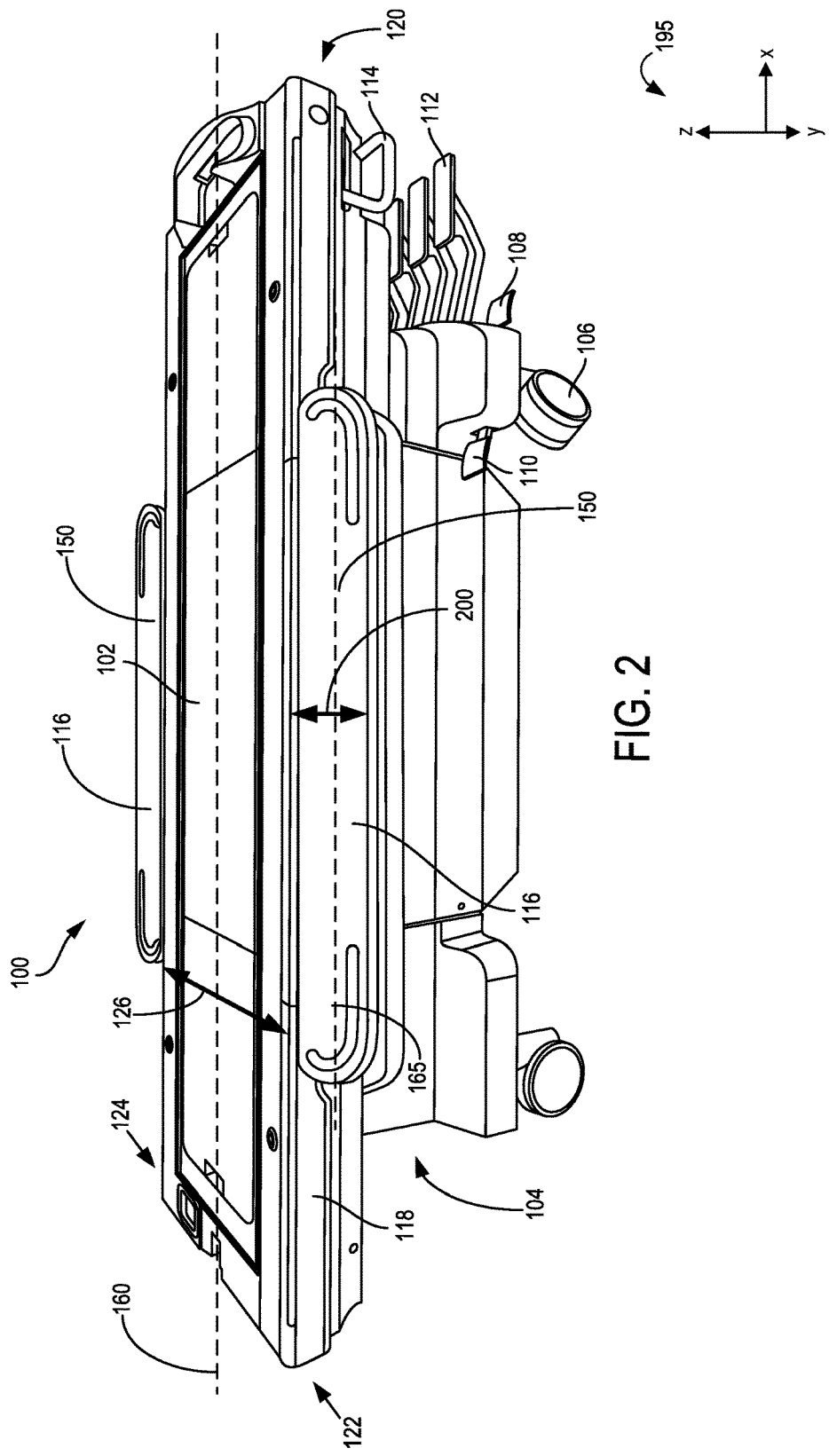
FIG. 2 shows a perspective view of the patient support table of FIG. 1 with the boards of the table adjusted to a partially raised position.

FIGS. 1-2 each show a table 100 including at least one adjustable board 116 (which may be referred to herein as armboard 116). Armboard 116 may be shaped to support an arm of a patient, in one example. As described above, in some examples table 100 may be a table for a magnetic resonance imaging (MRI) system and may be configured to support an object to be imaged by the MRI system (e.g., a patient). In other examples, the table 100 may be for a different type of system, such as a system for other imaging modalities or medical environments, as described above. Throughout the description below with reference to FIGS. 1-10, similar parts may be labeled similarly and not re-introduced after their initial introduction. References axes 195 are included by each of FIGS. 1-10 for relative comparison of the views shown.

Table 100 includes a top portion 120 including a top surface 102 (which may be referred to herein as a topmost surface) shaped to support the object to be imaged (e.g., a torso of a patient). Top portion 120 also includes side surfaces 118 positioned approximately perpendicular to the top surface 102 and joined with the top surface 102. Two armboards are coupled to the side surfaces (only one armboard 116 is visible in FIG. 1). The armboards 116 are pivotally coupled to the side surfaces 118 at each of a first side 122 and a second side 124 of the table 100, with the first side 122 being positioned opposite to the second side 124 across a width 126 of the table 100. Each armboard 116 includes a topmost surface 150, with topmost surface 150 shaped to support an arm of a patient. Each armboard 116 is configured to pivot relative to the top portion 120 as described below with reference to FIGS. 3-10. The top surface 102 of the table 100 and topmost surface 150 of the armboard 116 may each be planar surfaces (e.g., surfaces that are relatively flat and without curvature). The armboard 116 is positioned relative to the table 100 and rotated relative to the table 100 such that a longitudinal axis 165 of the armboard 116 is parallel to a longitudinal axis 160 of the table 100.

The top portion 120 is coupled (and supported by) a base 104. The base 104 includes casters 106 (e.g., wheels) in order to increase a mobility of the table 100. An operator (e.g., an MRI technician, PET technician, etc.) may actuate (e.g., press) a brake lever 108 of the table 100 in order to apply a braking force to one or more of the casters 106 in order to reduce a movement of table 100. The braking force may be released (e.g., removed) via actuation of a brake release lever 110. One or more gripping bars 114 may be coupled to the top portion 120 in order to increase a number of surfaces that the operator may interact with (e.g., push or pull) in order to move the table 100.

The table 100 additionally includes a plurality of pedals 112 for adjusting a tilt and/or position of the top portion 120 relative to the base 104. For example, one or more of the pedals 112 may be actuated (e.g., pressed) to increase or decrease a distance between the top portion 120 and the base 104, and/or one or more of the pedals 112 may be actuated to couple and/or decouple the table 100 with the MRI system (e.g., via a mechanically and/or electrically actuated locking mechanism).

FIG. 1 shows the armboards 116 in a lowered position relative to the top portion 120. In the lowered position, each armboard 116 is in a position vertically below the top surface 102 relative to the surface on which the table 100 sits and extends in a direction approximately parallel to the side surfaces 118. FIG. 2 shows the armboards 116 in a partially raised position relative to the top portion 120. In the position shown by FIG. 2, each armboard 116 extends in a direction approximately parallel with the top surface 102 and perpendicular with the side surfaces 118. By positioning the armboards 116 according to the example shown by FIG. 2, an effective width of the table 100 is increased. In the partially raised position, each armboard 116 extends a distance 200 away from the top surface 102.

Figure 3:
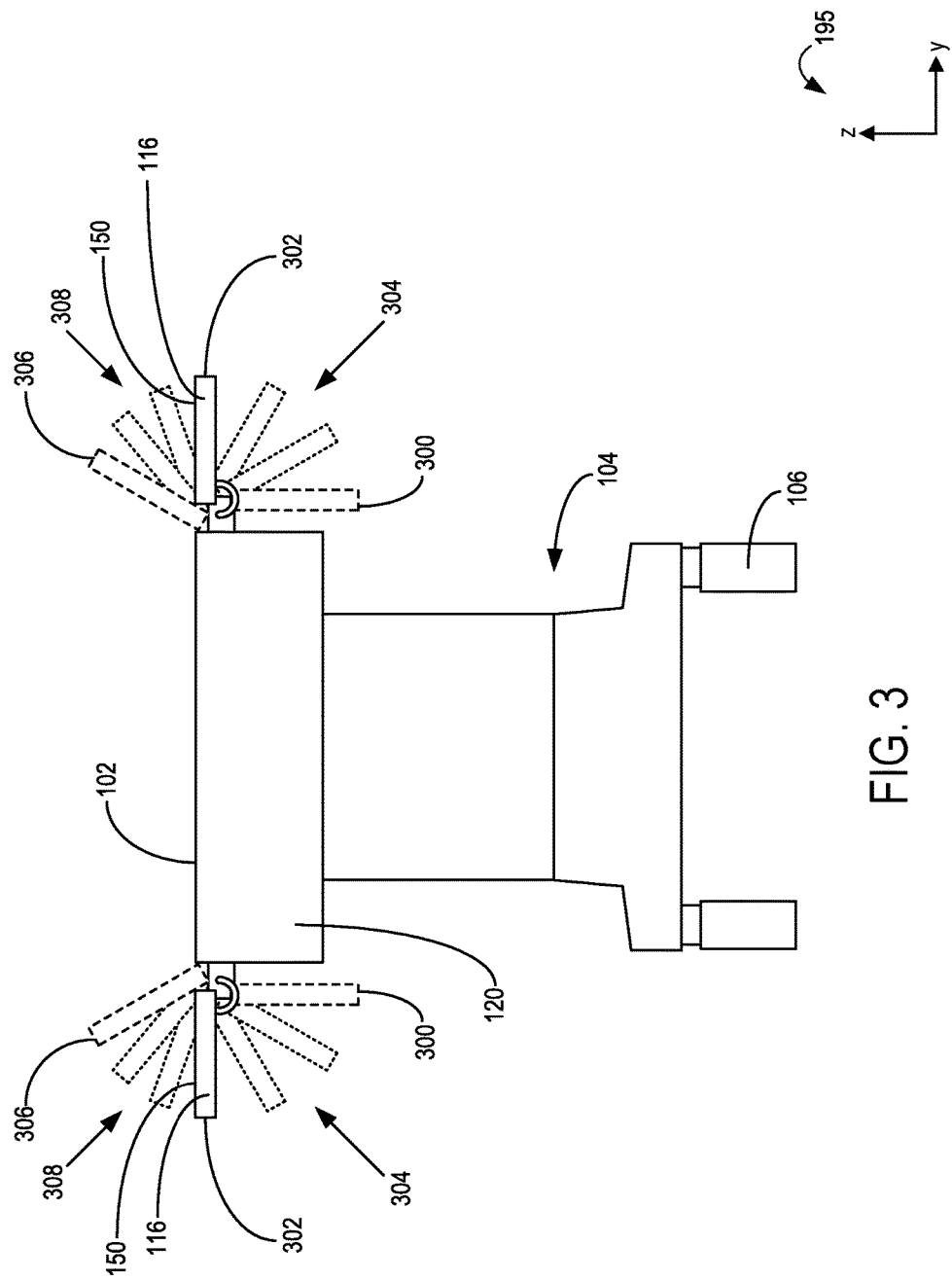
FIG. 3 schematically shows a side view of the patient support table including the boards adjusted to the fully lowered position, the partially raised position, a fully raised position, and a plurality of positions between fully lowered and fully raised.

FIG. 3 schematically shows a plurality of positions of the armboards 116 relative to the top portion 120. For example, a first position 300 (which may be referred to herein as a default position) corresponds to the fully lowered position of the armboards 116 shown by FIG. 1 and described above, and a second position 302 corresponds to the partially raised position of the armboards 116 shown by FIG. 2 and described above.

In the configurations described below with reference to FIGS. 4-10, the armboards 116 may be moved into a plurality of positions between the first position 300 and the second position 302 as indicated by arrow 304. The armboards 116 may additionally be moved into a third position 306 vertically above the second position 302, or moved into a plurality of positions between the second position 302 and the third position 306 as indicated by arrow 308. The armboards 116 may be locked into any of the positions described herein by a board adjustment assembly (which may be referred to herein as an armboard adjustment assembly), with examples of armboard adjustment assemblies shown by FIGS. 4-10 and described below. The third position 306 corresponds to a position in which at least a portion of the armboard 116 is vertically above the top surface 102 relative to the surface on which the table 100 sits. In one example, the armboard 116 may be at a 30 degree angle relative to the top surface 102 when the armboard 116 is in the third position 306, and the armboard 116 may be moved into any of the plurality of positions described above (e.g., indicated by arrow 304 and arrow 308). In one example, the armboard 116 may be moved into a position in which the armboard 116 is angled by 10 degrees relative to top surface 102 and is positioned partially above the top surface 102. In another example, the armboard 116 may be moved into a position in which the armboard is angled by 40 degrees relative to the top surface 102 and is positioned partially below the top surface 102. In yet another example, the armboard 116 may be moved away from the default position to each and any of at least three locked positions and any position between each of the at least three locked positions, as described below.

Although the first position 300, second position 302, and third position 306 are described above as example positions of the armboard 116, the above examples are non-limiting and the armboard 116 may be moved into any of a continuous plurality (e.g., continuous range) of positions between the first position 300 and third position 306. The armboard 116 may be moved into a plurality of positions via the various board adjustment assemblies described below with reference to FIGS. 4-10. The armboard 116 may be moved from an initial position corresponding to any position within the continuous plurality of positions to each and any of at least three undefined (e.g., variable) locked positions. For example, an initial locked position of the armboard 116 may correspond to a position in which the topmost surface 150 of the armboard 116 is angled relative to the top surface 102 of the table 100 by an amount (e.g., −25 degrees, 33 degrees, 17 degrees, etc.). The armboard 116 may be moved from the initial locked position to any other position of a continuous plurality of locked positions (e.g. moved to any position of the continuous plurality of locked positions, wherein the continuous plurality of locked positions includes each and any position at which an angle of the topmost surface 150 relative to the top surface 102 is any amount between 60 degrees and −90 degrees, for example). Each armboard 116 is retained in its position relative to the top portion 120 via an armboard adjustment assembly described below in various embodiments with reference to FIGS. 4-10.

Figure 4:
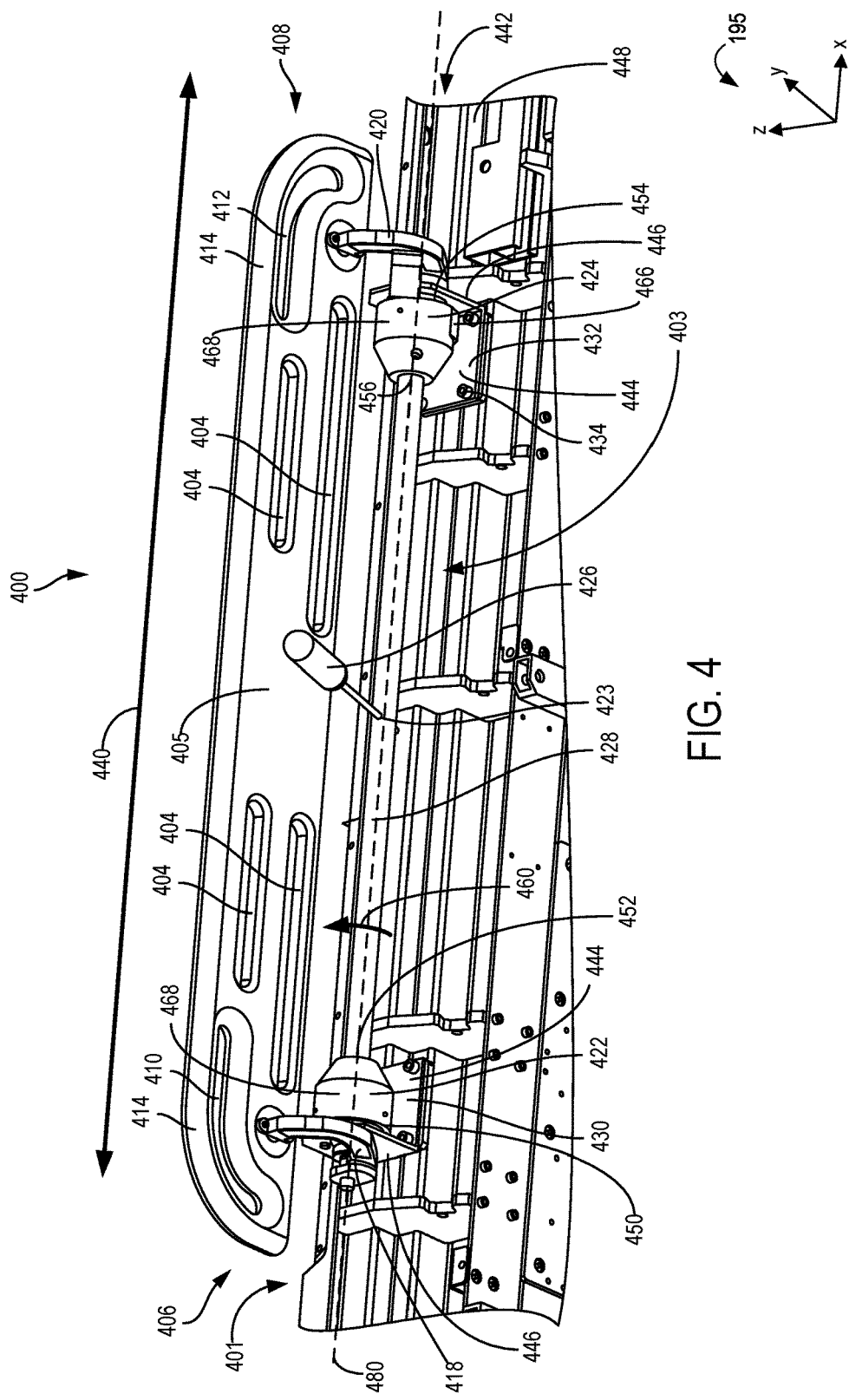
FIG. 4 shows a first perspective view of a first embodiment of a board adjustment assembly coupled to a board of a patient support table.

FIG. 4 shows a partial perspective view of a board 400 (which may be referred to herein as armboard 400) similar to the armboards 116 described above with reference to FIGS. 1-3. In the examples shown by FIGS. 4-7, a position of the armboards described is adjusted by board adjustment assemblies including a pair of one-way mechanical clutches. In some examples, the mechanical clutches may be wrapped spring clutches configured to allow the armboard to rotate upward but to prevent the armboard from rotating downward unless a lever or handle is actuated by an operator. The armboards are adjustable by the board adjustment assemblies (which may be referred to herein as armboard actuation devices or armboard adjustment assemblies) from a default position (e.g., a fully lowered position) through at least three locked positions (such as those shown by FIG. 3 and described above), wherein the armboard actuation device is configured to allow movement of the armboard from the default position to any of the at least three locked positions with a single actuation input (e.g., actuation of the appropriate lever or handle).

The armboard 400 is coupled to a table 401 similar to the table 100 shown by FIGS. 1-3 and described above via a board adjustment assembly 403 (which may be referred to herein as armboard adjustment assembly 403). Armboard 400 includes a first opening 410 positioned at a first side 406 and a second opening 412 positioned at a second side 408, with the first side 406 opposite to the second side 408 along a length 440 of the armboard 400. First opening 410 and second opening 412 may be shaped such that an operator (e.g., technician) may grip a surface 414 formed between each opening and an outer perimeter of the armboard 400 in order to re-position the armboard 400 (e.g., rotate the armboard upward or downward relative to a top portion 442 of table 401 as described above with reference to top portion 120 shown by FIGS. 1-3). A plurality of elongate grooves 404 may be formed by a bottom surface 405 of the armboard 400 and may increase a rigidity of the armboard 400. The armboard 400 additionally includes a topmost surface (not shown) similar to the topmost surface 150 of armboard 116 shown by FIGS. 1-3. In one example, the topmost surface of armboard 400 and the bottom surface 405 are arranged parallel to each other and are planar surfaces (e.g., surfaces that are approximately flat and without curvature). The armboard 400 is configured to rotate relative to the table 401 around a single axis of rotation 480.

In the embodiment shown by FIG. 4, armboard adjustment assembly 403 includes a first support 418, second support 420, first bracket 430, second bracket 432, first clutch 422, second clutch 424, connecting rod 428, and handle 426.

The bottom surface 405 of the armboard 400 is coupled to the first support 418 at the first side 406 and is coupled to the second support 420 at the second side 408. The first support 418 and second support 420 are each shaped in order to increase a rotational range of the armboard 400 around the top portion 442 of table 401. In one example, the first support 418 curves in a direction away from the bottom surface 405 and toward the first bracket 430 while the second support 420 curves in a direction away from the bottom surface 405 and toward the second bracket 432 when each support is coupled between the armboard 400 and the brackets (e.g., first bracket 430 and second bracket 432).

Each bracket includes a first surface 444 extending in a direction parallel with a side surface 448 of the top portion 442 (e.g., similar to side surfaces 118 described above with reference to FIGS. 1-3). Each bracket additionally includes a second surface 446 extending in a direction perpendicular to the side surface 448 and away from the side surface 448. The first surface 444 of each bracket is fixedly coupled (e.g., non-rotatably coupled) to the side surface 448 via a plurality of fasteners 434 (e.g., bolts). The second surface 446 of the first bracket 430 is coupled with the first support 418 such that the first support 418 is able to rotate relative to the first bracket 430. Similarly, the second surface 446 of the second bracket 432 is coupled with the second support 420 such that the second support 420 is able to rotate relative to the second bracket 432. In this way, the armboard 400, first support 418, and second support 420 rotate together around the single axis of rotation 480.

The first support 418 is coupled to a first end 450 of the first clutch 422 and the second support 420 is coupled to a first end 454 of the second clutch 424. In one example, a rod (shown by FIG. 5) may be inserted through an aperture of the first support 418 and the first end 450 of the first clutch 422 in order to couple the first support 418 to the first end 454 of the first clutch 422. The second support 420 may be coupled to the first end 454 of the second clutch 424 in a similar way.

A second end 452 of the first clutch 422 and a second end 456 of the second clutch 424 are each coupled to the connecting rod 428 such that the connecting rod 428 extends between the first clutch 422 and second clutch 424. The connecting rod 428 includes a handle 426 positioned at a midpoint 423 of the connecting rod 428 (e.g., a location halfway between the first clutch 422 and the second clutch 424 along the connecting rod 428). The handle may be directly coupled (e.g., fused and/or fastened) to the connecting rod 428 and may extend in a direction away from the connecting rod 428 and the table 401.

Each of the first clutch 422 and second clutch 424 are configured to normally allow the first support 418 and second support 420 to rotate upward (e.g., in a first direction 460) and to not allow the first support 418 and second support 420 to rotate downward (e.g., in a second direction opposite to the first direction 460). However, the first clutch 422 and second clutch 424 may allow the first support 418 and the second support 420 to rotate downward in response to actuation of the handle 426. In one example, an operator (e.g., technician) may actuate the handle 426 by applying a downward pressing force against the handle 426 in order to rotate the handle 426 in the downward direction. As the first support 418 and the second support 420 rotate upward or downward, the armboard 400 also rotates in the same direction as the rotation of the first support 418 and second support 420 due to the coupling of the armboard 400 to the first support 418 and second support 420.

In the examples shown by FIGS. 4-7, the first clutch 422 and the second clutch 424 are each wrapped spring clutches. The wrapped spring clutches are mechanical clutches that are mechanically actuated and are not electrically actuated. The first clutch 422 and the second clutch 424 each include a release tab 466 positioned along an exterior surface of a housing 468 of each clutch. The housing 468 of each clutch is rotationally coupled to the connecting rod 428 such that when the connecting rod 428 is rotated (e.g., via actuation of the handle 426 as described above), the housing 468 of each clutch rotates in a same direction as the connecting rod 428. By rotating the housing 468 of each clutch via the connecting rod 428, a friction force of a spring internal to each clutch may be released in order to rotate the armboard downward, as described below with reference to FIG. 5.

Figure 5:
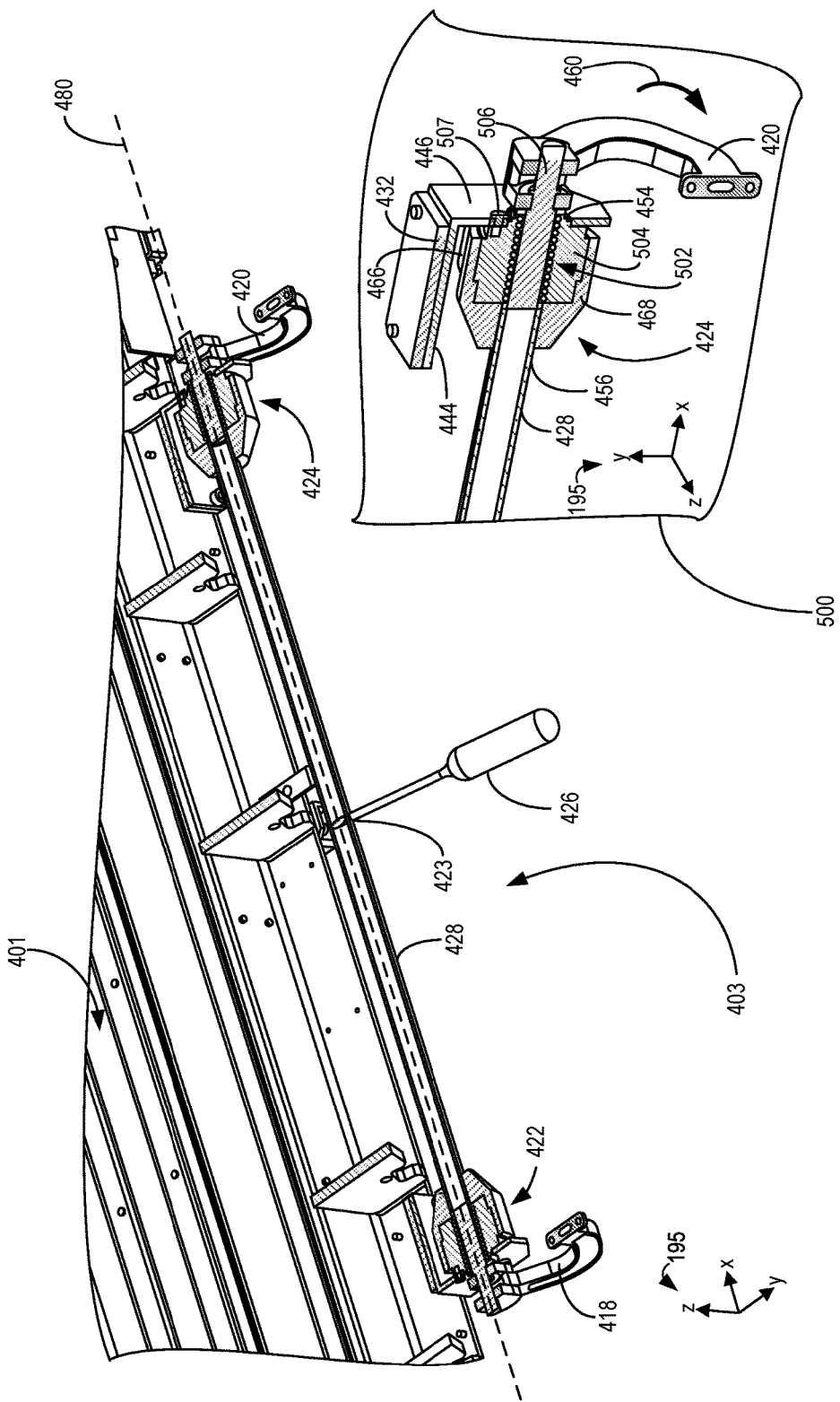
FIG. 5 shows a second perspective view of the first embodiment of the board adjustment assembly, with the board adjustment assembly shown in cross-section.

FIG. 5 shows another view of the table 401 and armboard adjustment assembly 403 shown by FIG. 4, with the armboard adjustment assembly 403 shown in cross-section. FIG. 5 additionally includes an inset 500 showing an enlarged view of the second clutch 424. The enlarged cross-sectional view of the second clutch 424 shown by inset 500 is intended to be representative of both first clutch 422 and second clutch 424. In other words, first clutch 422 includes similar components to those shown by the enlarged view of inset 500 and described below, with each of first clutch 422 and second clutch 424 operating in a similar manner.

As shown by inset 500, second clutch 424 includes housing 468 surrounding an interior portion 504 of the second clutch 424. As described above, the housing 468 may rotate in response to a rotation of the connecting rod 428 (e.g., in response to actuation of the handle 426). The housing 468 is coupled with the interior portion 504 of the second clutch 424 such that when the housing 468 is rotated, the interior portion 504 is not rotated. The interior portion 504 is fixedly coupled to the second surface 446 of the second bracket 432 by a fastener 507. The interior portion 504 is coupled with the second bracket 432 such that the interior portion 504 does not rotate relative to the second bracket 432.

A rod 506 is inserted into the first end 454 of the second clutch 424 and couples the second clutch 424 to the second support 420. A portion of the rod 506 is positioned within the interior portion 504 of the second clutch 424 and is surrounded along an outer perimeter of the rod 506 by a spring 502. Spring 502 is coupled with (and surrounded by) the interior portion 504 of the second clutch 424 such that the spring 502 does not rotate relative to the interior portion 504 of the second clutch 424.

As the second support 420 is rotated in the first direction 460 (e.g., an upward direction relative to the table 401), the rod 506 is also rotated in the first direction 460. The spring 502 is configured such that the rotation of the rod 506 in the first direction 460 applies an unwinding force to the spring 502. Friction between the rod 506 and the spring 502 resulting from the rotation of the rod 506 causes the spring 502 to slightly expand, thereby enabling the rod 506 and second support 420 to rotate freely in the first direction 460. However, attempting to rotate the second support 420 and rod 506 in a second direction opposite to the first direction 460 (e.g., a downward direction relative to the table 401) results in a tightening of the spring 502. Applying a force to the rod 506 in order to rotate the rod 506 in the second direction results in friction between the rod 506 and the spring 502 and causes the spring 502 to contract. The contraction of the spring 502 around the rod 506 prevents rotation of the rod 506 in the second direction due to the relatively high friction between the rod 506 and spring 502 as the spring 502 is contracted. As a result, the rod 506 is prevented from rotating in the second direction, thereby preventing the second support 420 from rotating in the second direction. In this way, the second clutch 424 (and first clutch 422, in a similar manner) enable a rotation of the armboard 400 (shown by FIG. 4) in the first direction 460 but do not allow rotation of the armboard 400 in the second direction (opposite to the first direction 460).

By configuring the armboard adjustment assembly 403 in this way, an operator (e.g., technician) or patient may raise the armboard 400 from the fully lowered position (e.g., as shown by armboard 116 of FIG. 1) to any position between the fully lowered position and the fully raised position (e.g., the third position 306 shown by FIG. 3). Additionally, if a load (e.g., an arm of a patient) is supported by the armboard 400, the armboard 400 may be raised gradually to a desired position without releasing the armboard 400 to rotate freely (e.g., without enabling the armboard 400 to rotate in the second direction), thereby increasing comfort of the patient and an amount of effort expended by the operator to adjust the armboard 400.

As described above with reference to FIG. 4, each of the clutches includes the release tab 466 positioned along the exterior surface of the housing 468. The release tab 466 is coupled to an end of the spring 502. As an example, when the housing 468 is rotated relative to the interior portion 504 of the second clutch 424 via rotation of the connecting rod 428 in the downward direction as described above (e.g., via actuation of the handle 426 as described above), the release tab 466 presses against the end of the spring 502 and causes the spring 502 to expand. As a result, friction between the spring 502 and the rod 506 is reduced, and the rod 506 and second support 420 are able to rotate downward in the second direction. Because the connecting rod 428 rotates the housing 468 on both of the first clutch 422 and the second clutch 424, the first support 418 is similarly able to rotate downward in the second direction when the handle 426 is actuated as described above. In this way, the handle 426 may be actuated in order to lower a position of the armboard 400 by allowing both of the first support 418 and second support 420 to rotate downward. However, when the handle 426 is not actuated, the armboard 400 is prevented from rotating downward, and the position of the armboard 400 is maintained by the frictional force between the rod and spring within the first clutch 422 and second clutch 424.

Figure 6:
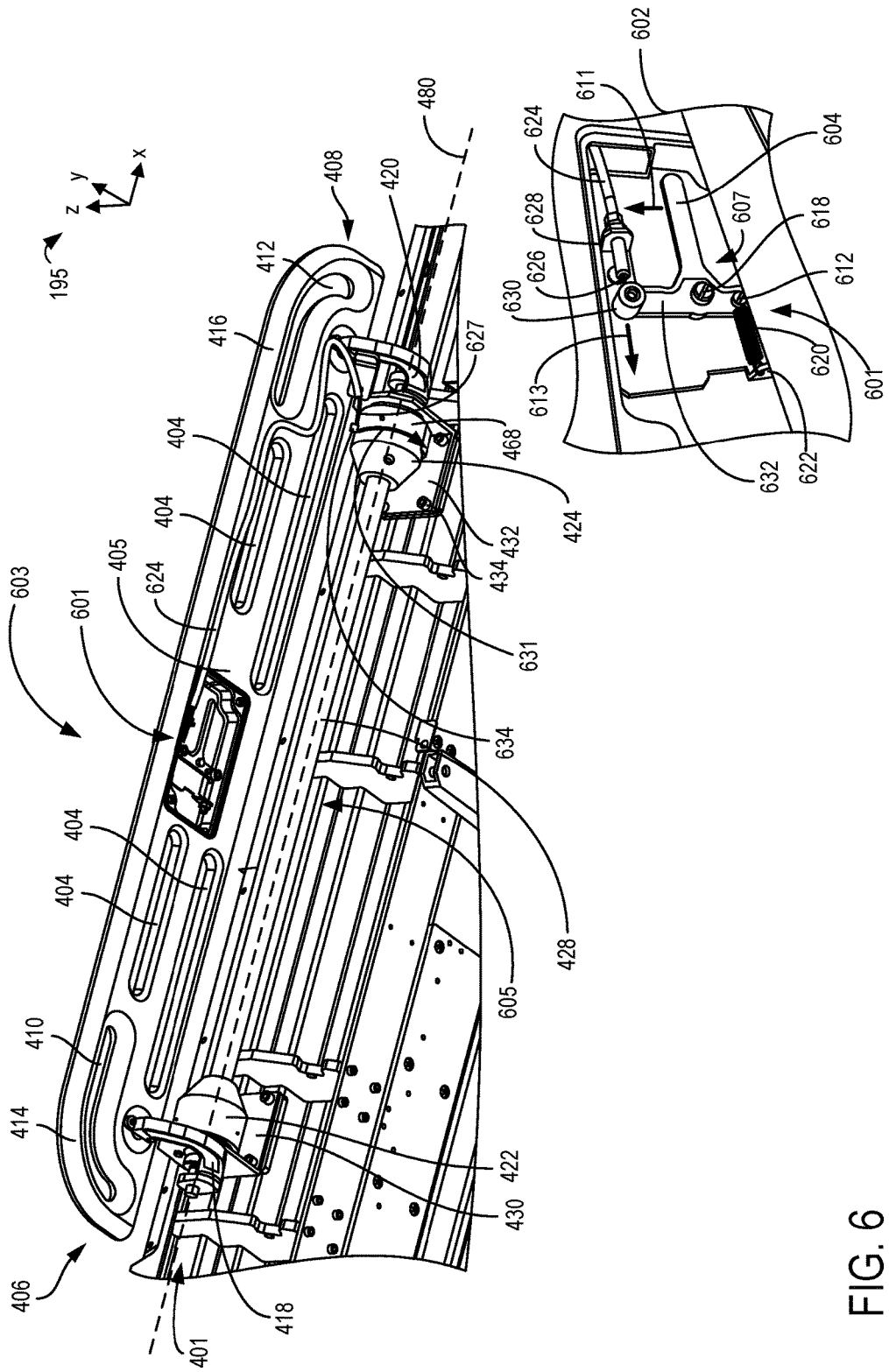
FIG. 6 shows a perspective view of a second embodiment of a board adjustment assembly coupled to a board of a patient support table.
Figure 7:
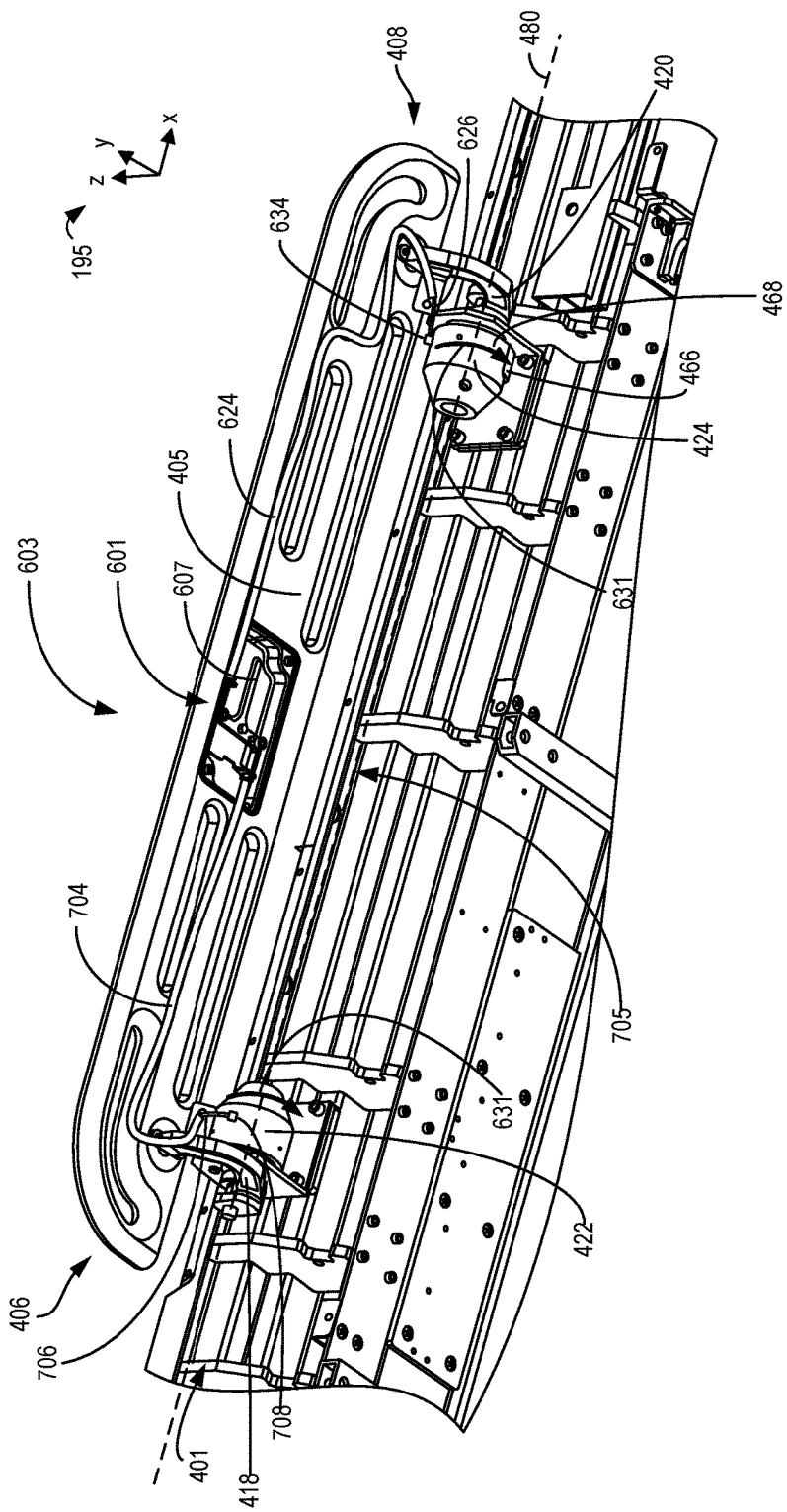
FIG. 7 shows a perspective view of a third embodiment of a board adjustment assembly coupled to the board of the patient support table.

In one example, the first clutch 422 and second clutch 424 may each be a wrapped spring clutch. In the example of the second clutch 424, an input hub (e.g., first end 454) is attached to a bracket (e.g., second support 420) that is attached to the armboard (e.g., armboard 400 shown by FIG. 4). The armboard is free to rotate in an upward direction (e.g., first direction 460). As the armboard rotates upward, the input hub is not connected to the output hub (e.g., second end 456). When the armboard is rotated in a downward direction, a spring (e.g., spring 502) tightens on the input hub and the output hub. As the spring tightens it connects the input hub to the output hub using friction which increases as the spring becomes tighter. This friction will hold up the armboard and prevent it from rotating in the downward direction. An output hub tang locks the output hub to the spring to prevent rotation of the output hub unless it is driven by input hub. To fold the armboard back down, a control tang (e.g., release tab 466 shown by FIG. 4) is pushed in the downward direction. When the control tang is pushed the spring will unwind which will eliminate the friction force that couples the input hub to the output hub. This allows the armboard to rotate freely from the fixed table side output hub. The input hub is attached to the armboard via the armboard attachment bracket (e.g., second support 420). The output hub is attached to a fixed side of the table (e.g., table 401). The ways to access to the control tang include (but are not limited to) connecting the control tang to a handle (e.g., lever 607, as shown by FIGS. 6-7) or having another mechanism such as a release bar (e.g., connecting rod 428) actuate the control tang. In either case, actuation of the handle (or the release bar) releases the spring and disconnects the input hub from the output hub so that the armboard can be folded down.

FIG. 6 shows a second embodiment of a board adjustment assembly 605 for a board 603 (which may be referred to herein as armboard adjustment assembly 605 and armboard 603, respectively). Armboard 603 is similar to armboard 116 shown by FIGS. 1-2 and armboard 400 shown by FIG. 4. However, armboard 603 includes a lever assembly 601 positioned within a center of the bottom surface 405 of the armboard 603. Although the armboard 400 shown by FIG. 4 and described above is not shown with a lever assembly 601, the armboard adjustment assembly 403 described above may also be utilized with an armboard such as armboard 603.

An enlarged view of lever assembly 601 is shown by inset 602. Lever assembly 601 includes a lever 607 with a first lever portion 604 and a second lever portion 632. The second lever portion 632 is positioned perpendicular relative to the first lever portion 604, and the lever 607 is coupled to the armboard 603 via a fastener 618 such that the lever 607 is able to rotate in a direction parallel with the bottom surface 405. The second portion 632 is coupled to a spring 620 via a fastener 612 at a first end and a cable 626 at a second end opposite to the first end. The spring 620 is additionally coupled to a stationary surface 622 of the lever assembly 601 and applies a first force to the second portion 632 of the lever 607 in order to restore the lever 607 to the position shown by FIG. 6 after the lever 607 has been actuated (as described below).

An operator (e.g., a technician) may apply a force to the lever 607 to rotate the first portion 604 of the lever 607 in a first direction 611. As the lever 607 rotates in the first direction 611, the spring 620 is expanded and the cable 626 is pulled in a second direction 613 due to the cable 626 being fastened to the second end of the lever 607 by a fastener 630. The cable 626 slides within a cable housing 624 coupled to the lever assembly 601 by a cable clamp 628. In one example, the cable housing 624 may be mounted to the bottom surface 405 of the armboard 603, and in other examples, the cable housing 624 may be routed through an interior of the armboard 603. As the cable 626 is pulled and slides within the cable housing 624, an end 627 of the cable 626 coupled to the housing 468 of the second clutch 424 via a fastener 634 rotates the housing 468 of the second clutch 424 in a downward direction 631 (e.g., a same direction as the second direction described above with reference to FIGS. 4-5). The housing 468 of the second clutch 424 is coupled to the connecting rod 428, and the connecting rod 428 is coupled to the housing 468 of the first clutch 422. As a result, rotating the housing 468 of the second clutch 424 in the downward direction 631 also rotates the connecting rod 428 and the housing 468 of the first clutch 422 in the downward direction 631.

As described above, rotating the housings 468 of the first clutch 422 and second clutch 424 presses the release tab 466 of each clutch against the corresponding spring internal to each clutch in order to expand the springs and enable the armboard 603 to rotate in the downward direction. In this way, the armboard 603 may rotate upward and not downward when the lever 607 is not actuated. Actuating the lever 607 (e.g., pulling the first portion 604 of the lever 607 in the first direction 611) allows the armboard 603 to rotate downward until the lever 607 is released, at which time the spring 620 returns the lever 607 to its non-actuated position.

FIG. 7 shows a third embodiment of a board adjustment assembly 705 (which may be referred to herein as armboard adjustment assembly 705) coupled to the armboard 603. Similar to the example described above with reference to FIG. 6, the armboard 603 includes the lever assembly 601 with a cable 626 sliding within a cable housing 624 to couple the lever 607 of the lever assembly 601 to the housing 468 of the second clutch 424.

The armboard adjustment assembly 705 shown by FIG. 7 does not include a connecting rod (e.g., connecting rod 428 shown by FIGS. 4-6) positioned between the first clutch 422 and second clutch 424. Instead, armboard adjustment assembly 705 includes a second cable 706 positioned within a second cable housing 704, with the second cable 706 coupled to the lever 607 at the first end of the second portion 632 of the lever 607 (e.g., second portion 632 shown by FIG. 6). In other words, instead of the spring 620 coupled to the first end of the second portion 632 as shown by FIG. 6, the second cable 706 is fastened to the first end in a similar manner as cable 626 is fastened to the second end of the second portion 632 of lever 607. The second cable housing 704 may be mounted to the bottom surface 405 of the armboard 603 or may be routed through the interior of the armboard 603, and an end of the cable 706 is coupled to the housing 468 of the first clutch 422 via a fastener 708.

Similar to the operation of the lever 607 as described above with reference to FIG. 6, the operator may actuate the lever 607 in order to rotate both of the housings 468 of the first clutch 422 and second clutch 424 in the downward direction 631. By rotating the housings 468 in the downward direction 631, the armboard 603 may be rotated downward as described above with reference to FIGS. 4-6. By utilizing the lever 607 to rotate the housings 468 of both clutches without a connecting rod, a size of the armboard adjustment assembly 705 may be reduced.

In the examples described above with reference to FIGS. 4-7, the armboards may be rotated into any of the positions described with reference to FIG. 3 via only a single actuation input. For example, with reference to the example shown by FIGS. 4-5, the single actuation input is the handle 426 coupled with the connecting rod 428. By actuating the single actuation input (e.g., actuating handle 426 as described above), the connecting rod 428 releases the frictional force (e.g., holding force) of each of the first clutch 422 and second clutch 424 in a synchronized manner. The first clutch 422 and second clutch 424 are thereby actuated simultaneously by the single actuation input. By configuring the armboard adjustment assembly in this way, each side of the armboard (e.g., first side 406 and second side 408) may be raised and/or lowered together in order to increase a supportive strength of the armboard. Because locking and unlocking the first clutch 422 and second clutch 424 is performed synchronously by releasing or actuating the single actuation input (respectively), each clutch may lock the position of the armboard with a relatively equal amount of force (e.g., frictional force as described above), and a response time of each clutch in response to adjustment from a locked condition to an unlocked condition (e.g., via actuation of the single actuation input) may be approximately equal.

In this way, an amount of force to actuate the single actuation input remains a same amount even with increased loading on the armboard. In a first example, the armboard may be in a first position and may support a first load of 25 lbs. In a second example, the armboard may be in the first position and may support a second load of 100 lbs. According to the examples described above, an amount of force required to actuate the single actuation input (e.g., the single actuation input of each embodiment described above, such as the handle 426 or the lever 607) is a same amount for both the first example and the second example. The armboard thereby is released from a locked condition to an unlocked condition by a same amount of force even with different amounts of loading. Additionally, because the armboard returns to a locked condition via synchronous locking of the clutches when the single actuation input is released (e.g., when the handle 426 and lever 607 of the corresponding embodiments are not actuated), and the armboard is locked into various positions without engagement of a pin within a hole (for example), the armboard adjustment assembly decreases an amount of force required to raise or lower the armboard (e.g., an amount of force required to actuate the single actuation input).

Figure 8:
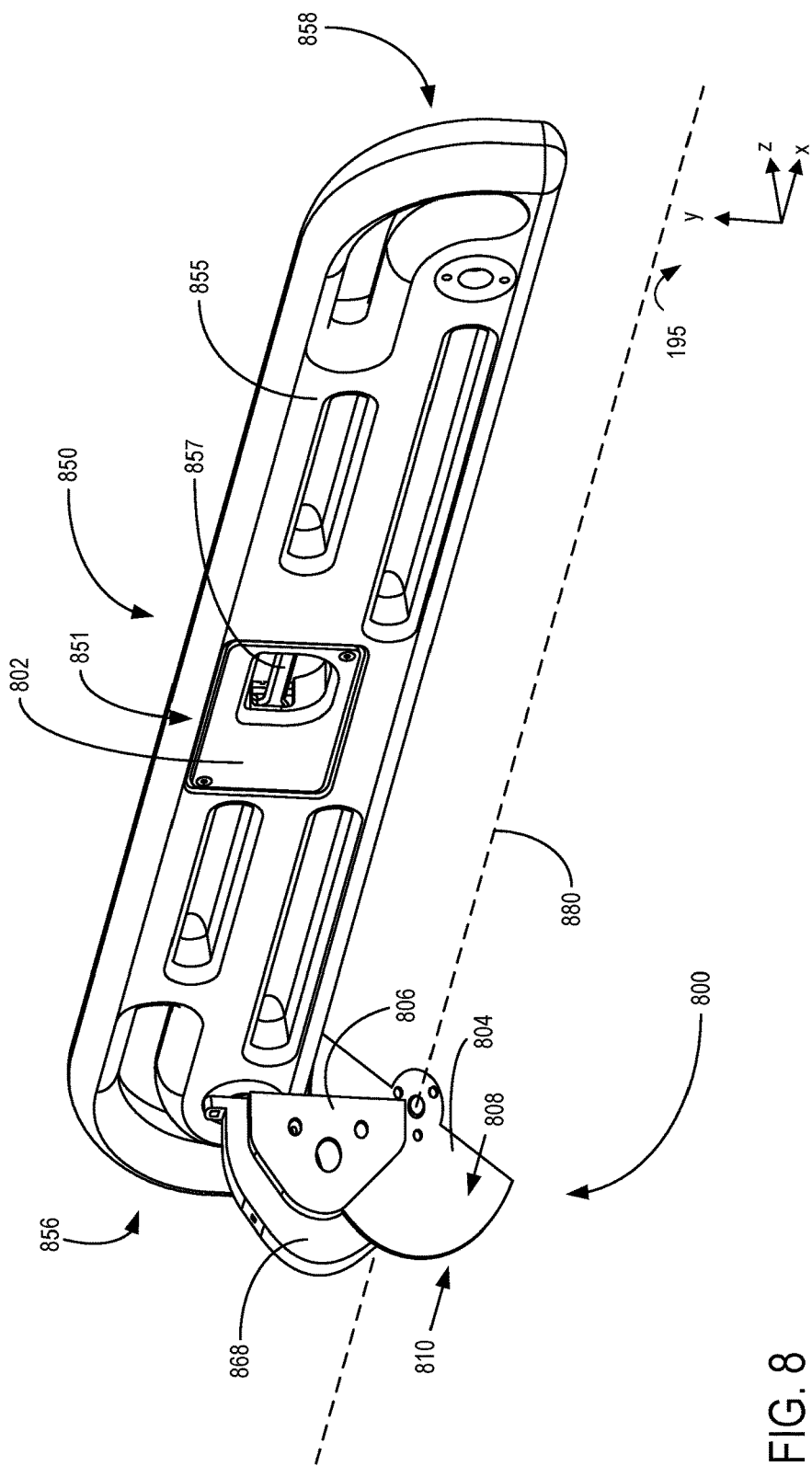
FIG. 8 shows a perspective view of a fourth embodiment of a board adjustment assembly coupled to the board of the patient support table.

FIG. 8 shows a fourth embodiment of a board adjustment assembly 800 coupled to a board 850 (e.g., similar to armboard 603 described above). Board adjustment assembly 800 and board 850 may be referred to herein as armboard adjustment assembly 800 and armboard 850, respectively. The armboard adjustment assembly 800 shown by FIGS. 8-10 includes a different mechanism for adjusting the position of the armboard 850. In particular, instead of the armboard 850 being adjusted via mechanical clutches as described above with reference to FIGS. 4-7, the armboard adjustment assembly 800 instead utilizes a pair of friction pads (described below) in order to prevent a rotation of the armboard 850 when an actuation input (e.g., lever) of the armboard adjustment assembly 800 is not actuated.

A lever assembly 851 (e.g., similar to lever assembly 601 shown by FIGS. 6-7) is shown to include a cover 802, and it is to be understood that the lever assembly 851 may be in either of the configurations described above with reference to lever assembly 601 of FIGS. 6-7. The example armboard adjustment assembly 800 shown by FIG. 8 includes components positioned only at a first side 856 (e.g., similar to first side 406 of armboard 400) of the armboard 850. However, alternate embodiments may include a similar arrangement of components at both the first side 856 and a second side 858 (e.g., similar to second side 408 of armboard 400) of the armboard 850. In such alternate embodiments, the lever assembly 851 may be in a configuration similar to that shown by FIG. 7 (e.g., a configuration in which two cables are coupled to the lever assembly 851), such that pulling a lever 857 (e.g., similar to lever 607 shown by FIGS. 6-7) actuates the armboard adjustment assembly 800 at both sides (e.g., first side 856 and second side 858) of the armboard 850.

Figure 9:
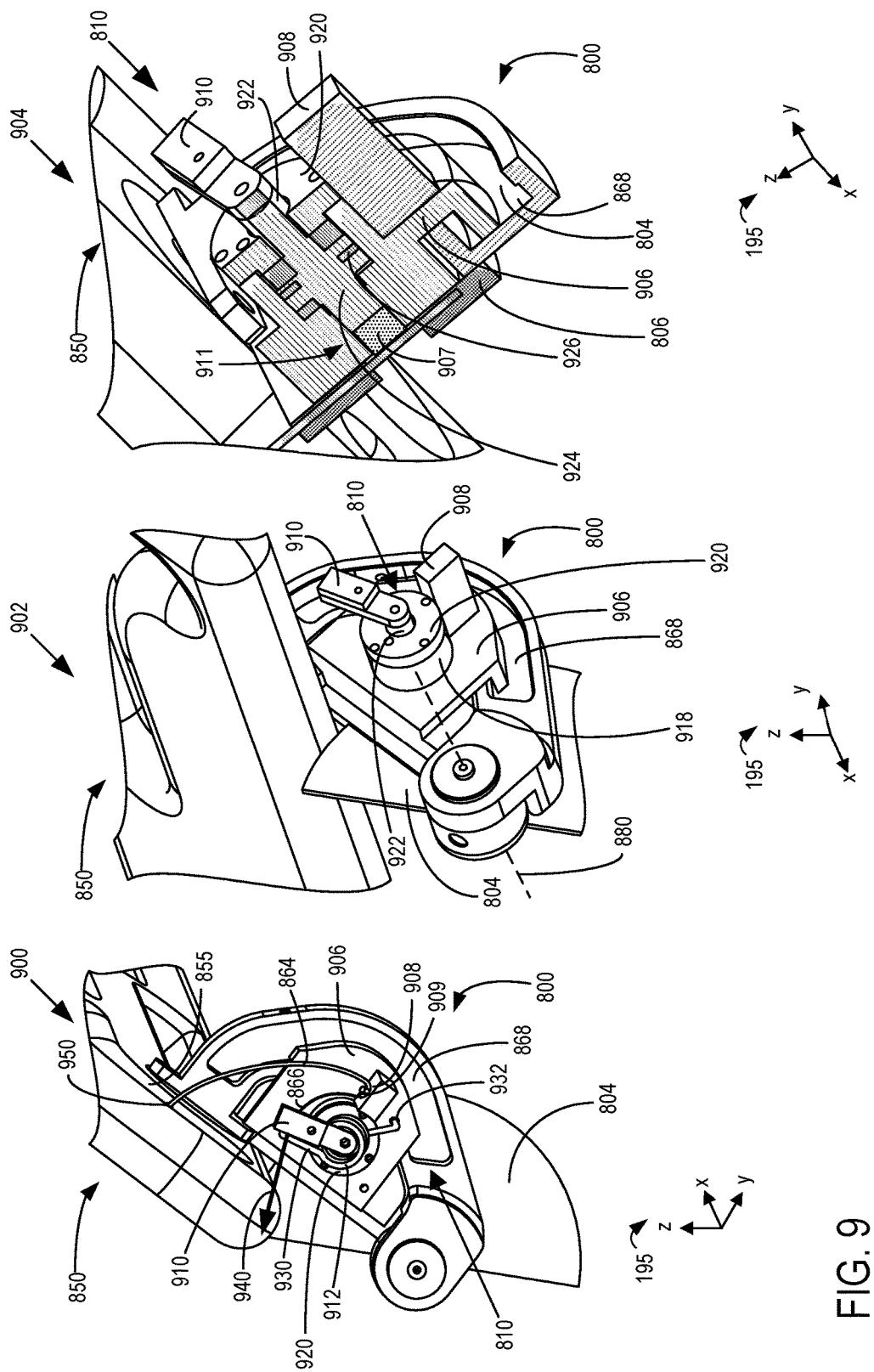
FIG. 9 shows three additional views of the fourth embodiment of the board adjustment assembly.
Figure 10:
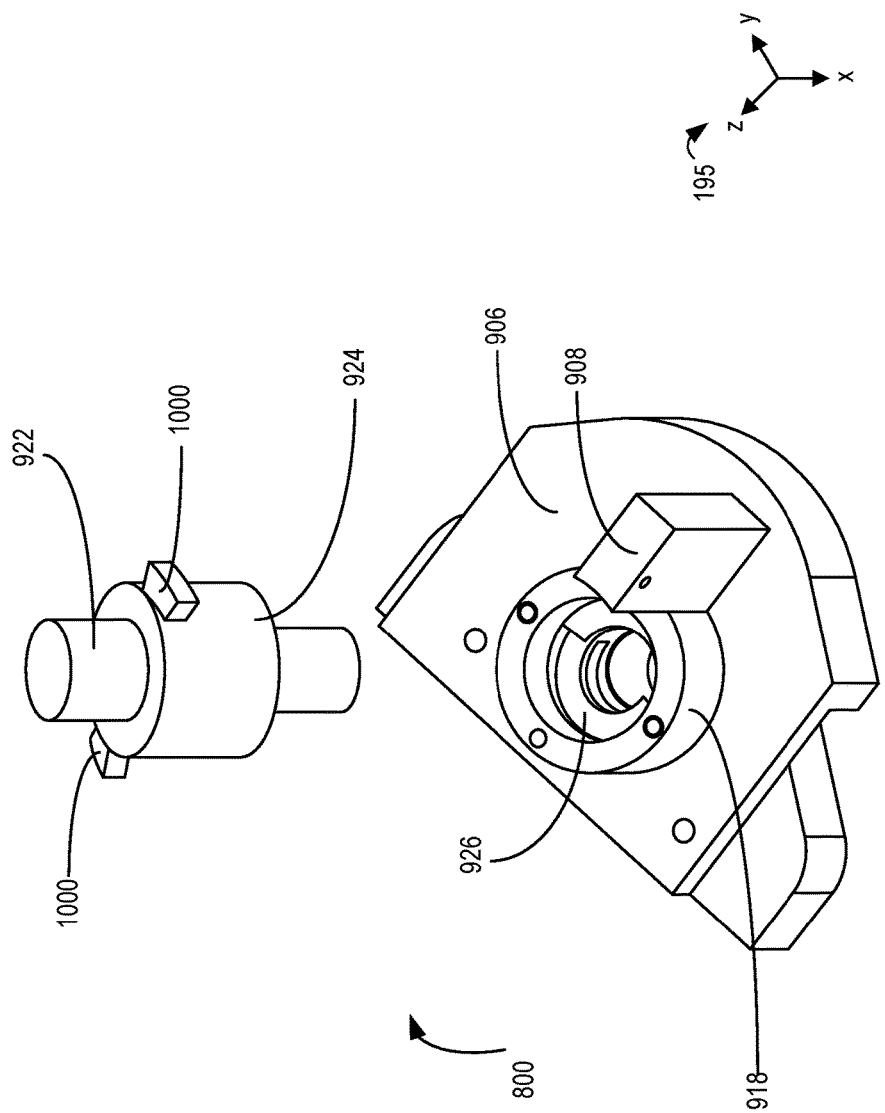
FIG. 10 shows an exploded view of components of the fourth embodiment of the board adjustment assembly.

In the example shown by FIGS. 8-9, the armboard adjustment assembly 800 includes a stationary surface 804 that is coupled to a table (e.g., table 100 shown by FIGS. 1-2) and does not rotate relative to the table (e.g., does not rotate relative to rotational axis 880 of the armboard 850). The armboard adjustment assembly 800 includes a first friction pad 806 positioned at a first side 808 of the stationary surface 804, and a number of components (described below with reference to FIGS. 9-10) are positioned at a second side 810 of the stationary surface 804.

FIG. 9 shows three different views of the second side 810 of the stationary surface 804. A first view 900 shows the full armboard adjustment assembly 800 including torsion spring 912, cable 866 (e.g., similar to cable 706 described above), and cable housing 864 (e.g., similar to cable housing 704 described above), while a second view 902 shows the armboard adjustment assembly 800 with the torsion spring 912, cable 866, and cable housing 864 removed. A third view 904 shows the armboard adjustment assembly 800 in cross-section.

The armboard adjustment assembly 800 includes a mount 906 positioned at the second side 810 of the stationary surface 804 and coupled to a first support 868 (e.g., similar to first support 418 of armboard 400). The first friction pad 806 (shown by FIG. 8) is mounted to the first support 868 such that the stationary surface 804 is positioned between the first friction pad 806 and mount 906. During conditions in which a position of the armboard 850 is not adjusted via the armboard adjustment assembly 800 (e.g., during conditions in which the lever 857 is not actuated by the operator), the first friction pad 806 and a second friction pad 907 press against the first side 808 and second side 810 (respectively) of the stationary surface 804. By pressing against the stationary surface 804, the first friction pad 806 and second friction pad 907 prevent the first support 868 from rotating due to frictional forces between both of the first friction pad 806 and the first side 808 of the stationary surface 804 and between the second friction pad 907 and the second side 810 of the stationary surface 804.

As shown by first view 900, armboard adjustment assembly 800 includes torsion spring 912 positioned at the second side 810 of the stationary surface 804. A first end 932 of torsion spring 912 is coupled to the mount 906 while a second end 930 of the torsion spring 912 is coupled to a cable clamp 910 such that the torsion spring 912 applies a biasing force to the cable clamp 910 in a first direction 940. The cable clamp 910 is coupled to a threaded insert 924 (shown by third view 904 and FIG. 10), and the threaded insert 924 is positioned within a reverse-threaded cylindrical bore 926 of the mount 906. The threaded insert 924 includes threads 1000 (shown by FIG. 10) shaped to fit within the reverse-threaded cylindrical bore 926 formed by extension 918 of the mount 906. The threaded insert 924 is coupled to the second friction pad 907 at a first end 911 of the threaded insert 924, and a second end 922 of the threaded insert protrudes from a cap 920 of the mount 906 and is coupled to the cable clamp 910. As the torsion spring 912 exerts the biasing force against the cable clamp 910 in the first direction 940, the threaded insert 924 is rotated further into the mount 906, thereby pressing the second friction pad 907 in a direction of the first side 808. The threaded insert 924 rotates and presses the second friction pad 907 against the stationary surface 804, and pressing the second friction pad 907 against the stationary surface 804 presses the first side 808 of the stationary surface 804 against the first friction pad 806. In this way, the armboard adjustment assembly 800 is configured to prevent a rotation of the first support 868 due to the biasing force of the torsion spring 912 against the cable clamp 910 (thereby pressing the brake pads against the stationary surface 804).

In order to adjust a position of the armboard 850, an operator may actuate (e.g., pull) lever 857 shown by FIG. 8. Lever 857 is coupled to cable 866 as described above with reference to FIG. 7. Cable 866 is positioned within cable housing 864, and cable housing 864 may be routed through an interior of the armboard 850. Cable housing 864 protrudes from a bottom surface 855 (e.g., similar to bottom surface 405) of armboard 850 and is fastened to cable mounting surface 908 via a fastener 909 (e.g., a bolt). The cable 866 is coupled to the cable clamp 910. When the lever 857 is actuated by the operator, the cable 866 exerts a force on the cable clamp 910 in a second direction opposite to the first direction 940. The force on the cable clamp 910 due to the cable 866 (e.g., due to actuation of lever 857) causes the threaded insert 924 to temporarily move in a direction away from the stationary surface 804 and mount 906 against the biasing force of the torsion spring 912. By moving the threaded insert 924 away from the stationary surface 804, the first friction pad 806 and second friction pad 907 do not press against the stationary surface 804 while the lever 857 is actuated. When the lever 857 is no longer actuated, the force due to the torsion spring 912 once again presses the brake pads against the stationary surface 804. In this way, the operator may actuate the lever 857 in order to adjust the position of the armboard 850, and may release the lever 857 in order to maintain a position of the armboard 850. As described above with reference to FIG. 3, the armboard adjustment assembly may maintain the armboard in any position of a continuous plurality of positions between fully lowered and fully raised, thereby increasing a versatility of the armboard.

By configuring the armboard adjustment assembly 800 according to the example described above with reference to FIGS. 8-10, the armboard may be raised and/or lowered without requiring an increased amount of actuation force even with increased loading. For example, in the embodiment shown by FIGS. 8-10, the lever 857 is the single actuation input of the armboard adjustment assembly 800. Actuation of the single actuation input enables the armboard 850 to raise or lower, and releasing the single actuation input does not allow the armboard 850 to raise or lower. A locking force of the armboard adjustment assembly 800 results from the biasing force of the torsion spring 912 and a friction force of the first friction pad 806 and second friction pad 907 against the stationary surface 804. Actuation of the single actuation input releases the friction force against the stationary surface 804, with a force of actuation of the single actuation input being larger than the biasing force of the torsion spring 912. For example, a threshold amount of force may be correspond to an amount of force applied to the torsion spring 912 in order to compress the torsion spring 912 and release the first friction pad 806 and second friction pad 907 from the stationary surface 804. The force of actuation may then be an amount of force greater than the threshold amount against the lever 857, with the threshold amount being a same amount of force for different amounts of load supported by the armboard 850. In this way, the force of actuation remains a same amount even with increased loading of the armboard.

A technical effect of the disclosure is to increase a number of available positions to which the armboard of the patient support table may be adjusted. By configuring the armboard adjustment assembly to support the armboard via one-way clutches (as described with reference to FIGS. 4-7) or via friction pads (as described with reference to FIGS. 8-10), the armboard may be rotated into (and maintained in) any position of a continuous range of positions between fully lowered and fully raised. Another technical effect of the disclosure is to utilize the armboard adjustment assembly to increase a reliability of the armboard. By configuring the armboard adjustment assembly to allow the armboard to rotate upward in a first direction and to not allow the armboard to rotate downward in a second direction until a handle/lever of the armboard adjustment assembly is actuated by the operator, the armboard may be maintained in a locked condition to prevent accidental downward rotation of the armboard. Additionally, because the armboard adjustment assembly may allow upward rotation of the armboard without actuation of the handle, an ease of use of the armboard is increased.

In one embodiment, a system for a patient support table includes: an armboard shaped to support an arm of a patient; and an armboard actuation device configured to adjust a position of the armboard relative to the patient support table, the armboard adjustable by the armboard actuation device from a default position through at least three locked positions, wherein the armboard actuation device is configured to allow movement of the armboard from the default position to any of the at least three locked positions with a single actuation input. In a first example of the system, the patient support table includes a first topmost surface shaped to support a torso of the patient, wherein the armboard includes a second topmost surface shaped to be in face-sharing contact with the arm of the patient, and wherein the default position comprises the second topmost surface being positioned at a first angle perpendicular to the first topmost surface and at least partially vertically below the first topmost surface relative to a surface on which the patient support table sits. A second example of the system optionally includes the first example, and further includes wherein the at least three locked positions comprises a first locked position in which the second topmost surface is positioned at a second angle relative to the first topmost surface and at least partially vertically below the first topmost surface, a second locked position in which the second topmost surface is positioned parallel to the first topmost surface, a third locked position in which the second topmost surface is positioned at a third angle relative to the first topmost surface and at least partially vertically above the first topmost surface, wherein the second angle is different than the first angle, and wherein the second topmost surface is adjustable to any angle between the first angle and third angle. A third example of the system optionally includes one or both of the first and second examples, and further includes wherein the armboard actuation device comprises a first mechanical clutch including a first end coupled to a first support of the armboard, wherein the first end is drivable in a first direction and not a second direction while the single actuation input is not actuated, wherein the first end is drivable in the first direction and the second direction while the single actuation input is actuated, and wherein the mechanical clutch is not electromechanically actuated. A fourth example of the system optionally includes one or more or each of the first through third examples, and further includes wherein the single actuation input includes an armboard lever coupled to a housing of the mechanical clutch by a cable, and wherein actuation of the armboard lever rotates the housing to unlock a position of the armboard. A fifth example of the system optionally includes one or more or each of the first through fourth examples, and further includes wherein the armboard actuation device further includes a second mechanical clutch including a second end coupled to a second support of the armboard, wherein the second end is drivable in the first direction and not the second direction while the single actuation input is not actuated, wherein the second end is drivable in the first direction and the second direction while the single actuation input is actuated, and wherein the second mechanical clutch is not electromechanically actuated. A sixth example of the system optionally includes one or more or each of the first through fifth examples, and further includes wherein the single actuation input includes a handle coupled to a connecting rod, the connecting rod coupled between a housing of the first mechanical clutch and a housing of the second mechanical clutch. A seventh example of the system optionally includes one or more or each of the first through sixth examples, and further includes wherein the armboard actuation device comprises: a mount coupled to a first pivotable support of the armboard, the mount including a threaded bore; a threaded insert shaped to fit within the threaded bore, the threaded insert including a first friction pad positioned at a first end of the threaded insert and a cable clamp positioned at a second end of the threaded insert; a stationary surface positioned between the first pivotable support and a second friction pad, the stationary surface directly coupled to the patient support table and the second friction pad coupled to the first pivotable support; and a torsion spring coupled to the mount and the cable clamp and configured to bias the threaded insert into the threaded bore. An eighth example of the system optionally includes one or more or each of the first through seventh examples, and further includes wherein the single actuation input is configured to bias the threaded insert away from the threaded bore. A ninth example of the system optionally includes one or more or each of the first through eighth examples, and further includes wherein the single actuation input includes an armboard lever mounted directly to the armboard, the armboard lever coupled to the cable clamp by a cable.

In one embodiment, an armboard adjustment assembly for a table includes: an armboard including a first side and second side; a first support coupled to the armboard at the first side; a second support coupled to the armboard at the second side; a first mechanical clutch including a first housing and a first end, the first end coupled to the first support; a second mechanical clutch including a second housing and a second end, the second end coupled to the second support; and a single linkage coupling the first housing to the second housing. In a first example of the armboard adjustment assembly, the single linkage comprises a connecting rod, and the connecting rod includes a handle directly coupled to the connecting rod. A second example of the armboard adjustment assembly optionally includes the first example, and further includes wherein the handle, connecting rod, first housing, and second housing are configured to rotate around a single rotational axis. A third example of the armboard adjustment assembly optionally includes one or both of the first and second examples, and further includes wherein the first housing includes a first clutch release tab and the second housing includes a second clutch release tab, and wherein the first clutch release tab and second clutch release tab are actuatable by rotation of the handle. A fourth example of the armboard adjustment assembly optionally includes one or more or each of the first through third examples, and further includes wherein the single linkage comprises an armboard lever coupled to the first housing by a cable, and wherein the first housing is coupled to the second housing by a connecting rod. A fifth example of the armboard adjustment assembly optionally includes one or more or each of the first through fourth examples, and further includes wherein the single linkage comprises an armboard lever, the armboard lever coupled to the first housing by a first cable and the armboard lever coupled to the second housing by a second cable.

In another embodiment, a system comprises: an armboard of a table, the armboard including a bottom surface, a first side, and a second side; a first pivotable support and a second pivotable support coupling the armboard to the table, the first pivotable support coupled to a first wrapped spring clutch and the second pivotable support coupled to a second wrapped spring clutch; and a connecting rod coupling a first housing of the first wrapped spring clutch to a second housing of the second wrapped spring clutch, the connecting rod rotatable by a handle. In a first example of the system, the first wrapped spring clutch includes a first spring coupled to the first pivotable support by a first rod, the second wrapped spring clutch includes a second spring coupled to the second pivotable support by a second rod, the first housing is coupled to a first end of the first spring, and the second housing is coupled to a second end of the second spring. A second example of the system optionally includes the first example, and further includes wherein the first spring is expandable by rotation of the first housing in a first direction and contractible by rotation of the first rod in a second direction, the second spring is expandable by rotation of the second housing in the first direction and contractible by rotation of the second rod in the second direction, and wherein contraction of the first spring locks a rotation of the first rod and first pivotable support and contraction of the second spring locks a rotation of the second rod and second pivotable support. A third example of the system optionally includes one or both of the first and second examples, and further includes wherein the handle is actuatable in the first direction to rotate the first housing and the second housing in the first direction.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for a patient support table, comprising:
a board shaped to support an arm of a patient; and
a board actuation device configured to adjust a position of the board relative to the patient support table, the board adjustable by the board actuation device from a default position through a plurality of locked positions, wherein the board actuation device is configured to allow movement of the board away from the default position to any of the locked positions with a single actuation input without requiring increased actuation force even with increased loading on the board,
wherein the board actuation device comprises a first mechanical clutch including a first end coupled to a first support of the board, wherein the first end is drivable in a first direction and not a second direction while the single actuation input is not actuated, wherein the first end is drivable in the first direction and the second direction while the single actuation input is actuated, and wherein the first mechanical clutch is not electromechanically actuated.

2. The system of claim 1, wherein the board is adjustable by the board actuation device from the default position through at least three locked positions, wherein the patient support table includes a first topmost surface shaped to support a torso of the patient, wherein the board includes a second topmost surface shaped to be in face-sharing contact with the arm of the patient, and wherein the default position comprises the second topmost surface being positioned at a first angle perpendicular to the first topmost surface and at least partially vertically below the first topmost surface relative to a surface on which the patient support table sits.

3. The system of claim 2, wherein the at least three locked positions comprise a first locked position in which the second topmost surface is positioned at a second angle relative to the first topmost surface and at least partially vertically below the first topmost surface, a second locked position in which the second topmost surface is positioned parallel to the first topmost surface, a third locked position in which the second topmost surface is positioned at a third angle relative to the first topmost surface and at least partially vertically above the first topmost surface, wherein the second angle is different than the first angle, and wherein the second topmost surface is adjustable to any angle between the first angle and the third angle.

4. The system of claim 1, wherein the single actuation input includes a board lever coupled to a housing of the first mechanical clutch by a cable, and wherein actuation of the board lever rotates the housing to unlock the position of the board.

5. The system of claim 1, wherein the board actuation device further includes a second mechanical clutch including a second end coupled to a second support of the board, wherein the second end is drivable in the first direction and not the second direction while the single actuation input is not actuated, wherein the second end is drivable in the first direction and the second direction while the single actuation input is actuated, and wherein the second mechanical clutch is not electromechanically actuated.

6. The system of claim 5, wherein the single actuation input includes a handle coupled to a connecting rod, the connecting rod coupled between a housing of the first mechanical clutch and a housing of the second mechanical clutch.

7. The system of claim 1, wherein the single actuation input includes a board lever mounted directly to the board, the board lever coupled to a cable clamp by a cable.

8. A board adjustment assembly for a table, comprising:
a board including a first side and a second side;
a first support coupled to the board at the first side;
a second support coupled to the board at the second side;
a first mechanical clutch including a first housing and a first end, the first end coupled to the first support;
a second mechanical clutch including a second housing and a second end, the second end coupled to the second support; and
a single linkage coupling the first housing to the second housing,
wherein the single linkage comprises a connecting rod, and wherein the connecting rod includes a handle directly coupled to the connecting rod, wherein the board is planar and positioned with its longitudinal axis parallel to a longitudinal axis of the table, and wherein the board rotates only about a single axis of rotation relative to the table while maintaining the longitudinal axes parallel to one another,
wherein the first housing includes a first clutch release tab and the second housing includes a second clutch release tab, and wherein the first clutch release tab and the second clutch release tab are actuatable by rotation of the handle.

9. The board adjustment assembly of claim 8, wherein the handle, the connecting rod, the first housing, and the second housing are configured to rotate around a single rotational axis.

10. A system comprising:
an armboard of a table, the armboard including a bottom surface, a first side, and a second side;
a first pivotable support and a second pivotable support coupling the armboard to the table, the first pivotable support coupled to a first wrapped spring clutch and the second pivotable support coupled to a second wrapped spring clutch; and
a connecting rod coupling a first housing of the first wrapped spring clutch to a second housing of the second wrapped spring clutch, the connecting rod rotatable by a handle,
wherein the first wrapped spring clutch includes a first spring coupled to the first pivotable support by a first rod, the second wrapped spring clutch includes a second spring coupled to the second pivotable support by a second rod, the first housing is coupled to a first end of the first spring, and the second housing is coupled to a second end of the second spring, and
wherein the first spring is expandable by rotation of the first housing in a first direction and contractible by rotation of the first rod in a second direction, the second spring is expandable by rotation of the second housing in the first direction and contractible by rotation of the second rod in the second direction, and wherein contraction of the first spring locks a rotation of the first rod and the first pivotable support and contraction of the second spring locks a rotation of the second rod and the second pivotable support.

11. The system of claim 10, wherein the handle is actuatable in the first direction to rotate the first housing and the second housing in the first direction.

* * * * *